United States Patent [19]

Bradford et al.

[11] Patent Number: Plant 6,675

[45] Date of Patent: Mar. 14, 1989

[54] NECTARINE TREE (SPARKLING MAY)

[76] Inventors: Norman G. Bradford, 11875 E. Savana Rd.; Lowell G. Bradford, 12439 E. Savana Rd., both of Le Grand, Calif. 95333

[21] Appl. No.: 122,267

[22] Filed: Nov. 16, 1987

[51] Int. Cl.[4] ..... A01H 5/00

[52] U.S. Cl. ..... Plt./41

[58] Field of Search ..... Plt./41

[56] References Cited

U.S. PATENT DOCUMENTS

| | | | |
|---|---|---|---|
| P.P. 4,792 | 11/1981 | Anderson | Plt. 41 |
| P.P. 5,454 | 4/1985 | Bradford | Plt. 41 |
| P.P. 5,538 | 4/1985 | Bradford | Plt. 41 |

*Primary Examiner*—James R. Feyrer

[57] ABSTRACT

The present invention relates to a nectarine tree and more particularly to a new and distinct variety broadly characterized by a medium size, vigorous, hardy, productive and regular bearing tree. The fruit matures under the ecological conditions described approximately the first week in June, with first picking on June 6, 1987. The fruit is of uniform medium size, very firm making excellent quality for keeping and shipping, full red in skin color, and sweet subacid flavor. The variety was developed as the result of a seedling of Red Diamond (U.S. Plant Pat. No. 3,165) as the seed parent and Aurora Grand (U.S. Plant Pat. No. 4,792) as the selected pollen parent. Subsequent to origination of the present variety of nectarine tree, we asexually reproduced it by budding and grafting, and such reproduction of plant and fruit characteristics were true to the original plant in all respects.

1 Drawing Sheet

BACKGROUND OF THE VARIETY

The present variety of nectarine tree was produced by us at Bradford Farms in Merced County (San Joaquin Valley), Calif., as the result of a seedling of Red Diamond (U.S. Plant Pat. No. 3,165) as the seed parent and Aurora Grand (U.S. Plant Pat. No. 4,792) as the selected pollen parent. Subsequent to origination of the present variety of nectarine tree, we asexually reproduced it by budding and grafting, and such reproduction of plant and fruit characteristics were true to the original plant in all respects.

The present variety most nearly resembles the May Diamond (U.S. Plant Pat. No. 5,454) in appearance by being a full red colored freestone with excellent firmness, but is distinguished therefrom and an improvement thereon by harvesting seven days earlier. This earlier ripening time fills a very important harvesting time gap between Early Diamod (U.S. Plant Pat. No. 5,438) and May Diamond for commercial nectarines in central California.

The present variety is similar to its seed parent, Red Diamond, by being a full colored firm freestone but is distinguished therefrom by ripening 29 days earlier. The present variety is similar to its pollen parent, Aurora Grand, by being a full colored early ripening freestone but is distinguished therefrom by ripening 3 days earlier, by being more uniform in both size and ripening, and by having a recessed apex.

DRAWING

The accompanying photograph shows the characteristics of the whole fruit in skin color and form, a characteristic fruit divided on its suture plane showing the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of eating ripe on June 10, 1987. All major color code designations are by reference to the Inter-Society Color Council, National Bureau of Standards. Common color names are also used occasionally.

TREE

Size: Medium.
Vigor: Vigorous.
Growth: Spreading and dense.
Form: Vase-shaped.
Hardiness: Hardy.
Production: Productive.
Bearing: Regular bearer.
Trunk:
- *Size.*—Medium.
- *Texture.*—Medium.
- *Color.*—Dark grayish reddish brown [47. d.gy.rBr].
- *Lenticels.*—Numerous. Color: Light brown [57. l.Br]. Size: 1/16" to ¼", [1.588–6.350 mm.].

Branches:
- *Size.*—Medium.
- *Texture.*—Medium.
- *Color.*—1st Year Wood — Topside: Grayish red [19. gy.R]. 1st Year Wood — Underside: Brillant yellow green [116. brill. YG]. Older Wood: Grayish reddish brown [46 gy.rBr].
- *Lenticels.*—Numerous, small.

Leaves:
- *Size.*—Medium. Average Length: 5.75" [146.05 mm.]. Average Width: 1½" [38.1 mm.].
- *Thickness.*—Medium.
- *Form.*—Elliptical.
- *Apex.*—Acuminate.
- *Base.*—Acute.
- *Surface.*—Smooth.

*Color.*—Dorsal Surface: Medium olive green [125. m.OlG]. Ventral Surface: Medium yellow green [120. m.YG].

*Margin.*—Finely serrate.

*Venation.*—Pinnately net veined.

*Petiole.*—Medium length and thickness. Average Length: 7/16" [11.1 mm.]. Average Thickness: 1/16" [1.587 mm.].

*Glands.*—Numbers: 2 to 6 per leaf. Position: Most oppositely but some alternately positioned on petiole and base of blade. Size: Medium. Form: Reniform. Color: Pale yellow green [121. p.YG] with some Grayish red [19. gy.R] tinting.

*Stipules.*—Numerous. Length: ¼" [6.35 mm.].

Flower Buds:

*Hardiness.*—Hardy.

*Size.*—Medium.

*Length.*—Medium.

*Form.*—Free.

*Surface.*—Pubescent.

Flowers:

*Blooming period.*—Medium, as compared with other varieties.

*Size.*—Small.

*Color.*—Moderate pink [5 m.Pk].

FRUIT

Maturity when described: Eating Ripe, June 10, 1987.

Date of first picking: June 6, 1987.

Date of last picking: June 12, 1987.

Size: Uniform, medium.

*Average Diameter Axially.*—2⅝" [66.68 mm].

*Average Traversely in Suture Plane.*—2⅜" [60.33 mm].

Form: Uniform, symmetrical, and slightly oblong.

*Longitudinal section form.*—Oval.

*Transverse section through diameter.*—Round.

Suture: Shallow, extends from base to beyond the apex, and has a medium depression beyond the pistil point.

Ventral surface: Rounded and slightly lipped throughout.

Lips: Slightly unequal.

Cavity: Flaring, elongated in the suture plane with suture showing on both sides.

Base: Slightly cuneate and truncate.

Apex: Very short, of negligible length, depressed.

Pistil point: Some oblique and some apical.

Stem: Medium.

*Average length.*—⅜" [9.525 mm].

*Average width.*—⅛" [3.175 mm.].

Skin:

*Thickness.*—Medium.

*Texture.*—Medium.

*Tenacity.*—Tenacious to flesh.

*Tendency to crack: None observed as of yet.*

*Color.*—Deep red [13. deep R] over the entire surface.

Flesh:

*Color.*—Light yellow [86. 1.Y] from skin to pit.

*Surface of the pit cavity.*—Covered with pale greenish yellow [104. p.gY] fibers.

*Amygdalin.*—Moderate.

*Juice.*—Abundant.

*Texture.*—Firm, fine, crisp.

*Fibers.*—Few, fine.

*Ripens.*—Evenly.

*Flavor.*—Subacidic, with abundant sugar.

*Aroma.*—Mild.

*Eating quality.*—Very good.

STONE

Type: Freestone.

Form: Oval.

Base: Straight.

Apex: Mucronate.

Sides: Slightly unequal.

Surface: Irregularly furrowed throughout with pitting toward base and ridges generally closer to the apex.

Ridges: Jagged.

Color: Pale Orange Yellow [73. p.OY].

Pit wall: ¼" [6.35 mm.] thick.

Tendency to split: Slight.

Kernel:

*Form.*—Obovate.

*Taste.*—Sweet.

*Viable.*—Yes.

*Average width.*—7/16" [11.11 mm.].

*Average length.*—11/16" [17.462 mm.].

Pellicle: Color: Pale yellow [89 p.Y].

Amygdalin: Scant.

USE

Market: Fresh and long distance shipping.

Keeping quality: Good to excellent.

Shipping quality: Good to excellent.

Resistance to insects: No unusual susceptibilities noted.

Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct early ripening variety of freestone nectarine tree, substantially as illustrated and described, which most nearly resembles the May Diamond (U.S. Plant Pat. No. 5,454) variety but is distinguished from and an improvement on that variety by ripening seven days earlier, by having a sweeter less acidic flavor, and by blooming more densely the fruit has average size, good flavor, good firmness, and excellent shape for the commercial grower also, the fruit harvests in California at a very desirable time period, approximately halfway between Early Diamond (U.S. Plant Pat. No. 5,438) and May Diamond (U.S. Plant Pat. No. 5,454).

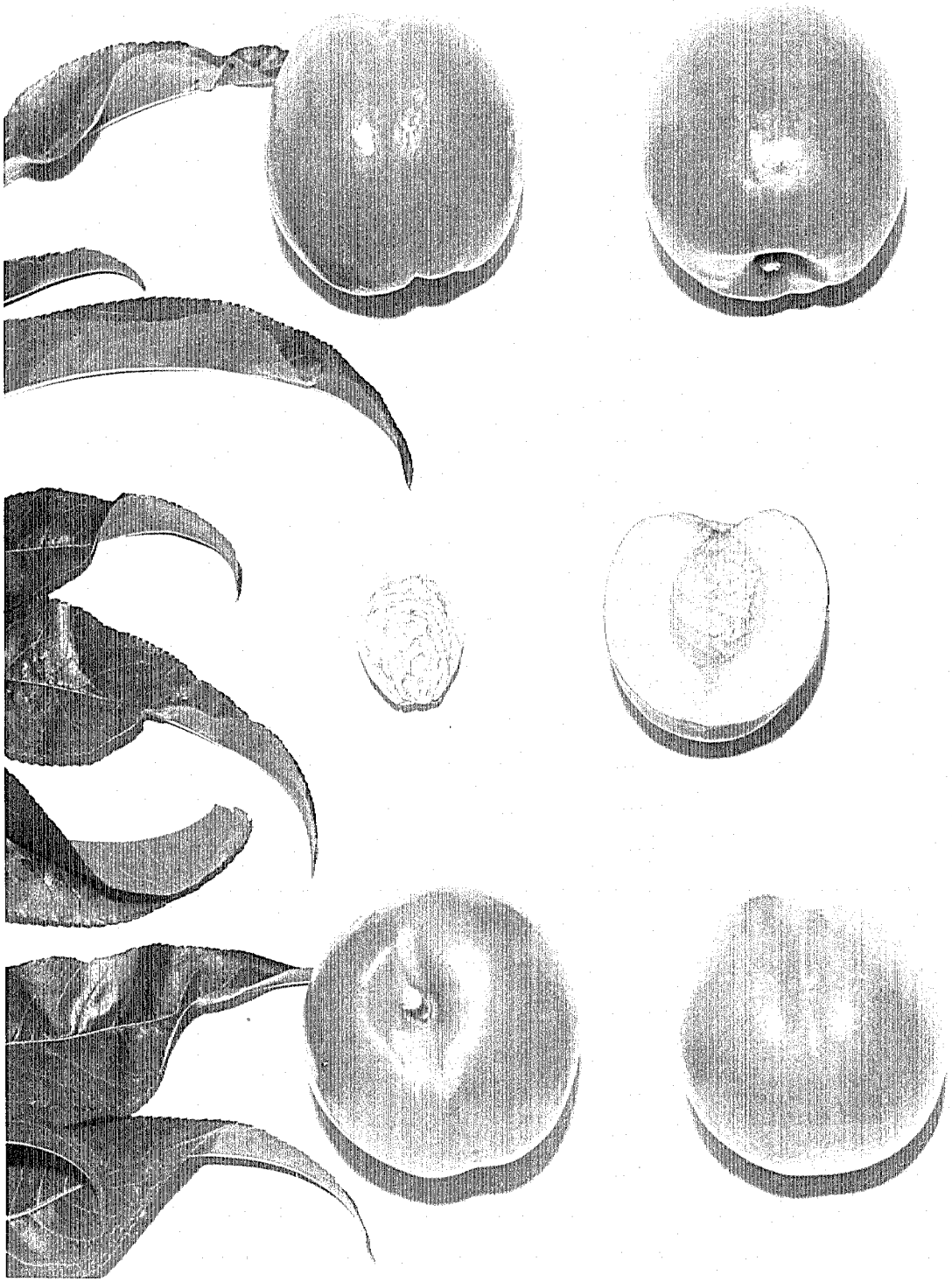

* * * * *